United States Patent
Franzke et al.

(10) Patent No.: US 10,126,221 B2
(45) Date of Patent: Nov. 13, 2018

(54) MEASURING ARRANGEMENT FOR RADIOMETRIC DENSITY- OR FILL LEVEL MEASURING OF A MEDIUM IN A MEASURING TUBE

(71) Applicant: Endress + Hauser GmbH + Co. KG, Maulburg (DE)

(72) Inventors: Markus Franzke, Schworstadt-Dossenbach (DE); Axel Schumann, Lorrach (DE); Michael Schmidt, Schopfheim (DE); Dirk Glaser, Steinen (DE)

(73) Assignee: ENDRESS+HAUSER SE+CO.KG, Maulburg (DE)

( * ) Notice: Subject to any disclaimer, the term of this patent is extended or adjusted under 35 U.S.C. 154(b) by 0 days.

(21) Appl. No.: 15/537,896

(22) PCT Filed: Dec. 1, 2015

(86) PCT No.: PCT/EP2015/078204
§ 371 (c)(1),
(2) Date: Jun. 20, 2017

(87) PCT Pub. No.: WO2016/102156
PCT Pub. Date: Jun. 30, 2016

(65) Prior Publication Data
US 2018/0136103 A1 May 17, 2018

(30) Foreign Application Priority Data
Dec. 22, 2014 (DE) .................. 10 2014 119 414

(51) Int. Cl.
*G01N 9/24* (2006.01)
*G01F 23/288* (2006.01)

(52) U.S. Cl.
CPC ............. *G01N 9/24* (2013.01); *G01F 23/288* (2013.01)

(58) Field of Classification Search
CPC ......... G01F 23/288; G01N 23/09; G01N 9/24
See application file for complete search history.

(56) References Cited

U.S. PATENT DOCUMENTS

| 4,425,803 A | 1/1984 | Baumoel |
| 4,454,767 A | 6/1984 | Shinkai |

(Continued)

FOREIGN PATENT DOCUMENTS

| DE | 102014119414 A1 | 6/2016 |
| JP | 10221137 A | 8/1998 |

OTHER PUBLICATIONS

German Search Report, German Patent Office, Munich, DE, dated Sep. 14, 2015.

(Continued)

*Primary Examiner* — David Porta
*Assistant Examiner* — Faye Boosalis
(74) *Attorney, Agent, or Firm* — Bacon & Thomas, PLLC

(57) ABSTRACT

A measuring arrangement for radiometric density-or fill level measurement of a medium in a measuring tube in the field of automation technology. The measuring arrangement is composed of a radioactive radiation source, a detector unit and a clamping apparatus for the radiation source as well as the detector unit. The invention is distinguished by features including that the clamping apparatus has blocking elements, which make the radiation cone of the radioactive radiation source between the measuring tube and the clamping apparatus laterally inaccessible. In such case, the blocking elements are arranged in such a manner that the mea- (Continued)

suring arrangement is suitable for different diameters of the measuring tube, without the blocking elements losing their protective action.

10 Claims, 2 Drawing Sheets

(56) References Cited

U.S. PATENT DOCUMENTS

| | | | | |
|---|---|---|---|---|
| 4,794,256 | A | * 12/1988 | DiMartino | ............ G01F 23/288 |
| | | | | 250/357.1 |
| 6,026,693 | A | * 2/2000 | Baumoel | ................ G01F 1/662 |
| | | | | 73/861.27 |
| 6,084,243 | A | 7/2000 | Smith, Jr. | |
| 2009/0025487 | A1 | 1/2009 | Gysling | |
| 2011/0168899 | A1 | 7/2011 | Cheshire | |
| 2018/0136103 | A1 | 5/2018 | Franzke | |

OTHER PUBLICATIONS

International Search Report, EPO, The Netherlands, dated Jun. 17, 2016.
English Translation of the International Preliminary Report on Patentability, WIPO, Geneva, CH, dated Jul. 6, 2017.

* cited by examiner

MEASURING ARRANGEMENT FOR RADIOMETRIC DENSITY- OR FILL LEVEL MEASURING OF A MEDIUM IN A MEASURING TUBE

TECHNICAL FIELD

The invention relates to a measuring arrangement for radiometric density- or fill level measuring of a medium in a measuring tube.

BACKGROUND DISCUSSION

In automation technology, especially in process automation technology, field devices are often applied, which serve for registering and/or influencing process variables. Serving for registering process variables are sensors, which, for example, are integrated in fill level measuring devices, flow measuring devices, pressure- and temperature measuring devices, pH redox potential measuring devices, conductivity measuring devices, density measuring devices, etc. for registering the corresponding process variables, fill level, flow, pressure, temperature, pH value, redox potential, conductivity, and density. Serving for influencing process variables are actuators, such as, for example, valves or pumps, via which the flow of a liquid in a pipeline section or the fill level in a container can be changed. Referred to as field devices are, in principle, all devices, which are applied near to the process and deliver, or process, process relevant information. In connection with the invention, the terminology, field devices, thus includes also remote I/Os, radio adapters, and, generally, electronic components, which are located at the field level. A large number of such field devices are manufactured and sold by the firm, Endress+Hauser.

Often, radiometry is applied as a measuring method, such as, for example, in the case of a density-or fill level measurement. In the case of a density-and fill level measurement, the measuring method is based on radioactive radiation, preferably gamma radiation, which is emitted from a radiation source and allowed to pass through the medium to be measured. After passage through the medium, the transmitted radiation intensity is measured by a detector unit. By relating the transmitted radiation intensity to original intensity of the radiation source, the density of the medium or the fill level of the medium in the pipe can be deduced. The measuring principle has proved itself especially for density determination of media with high density, which are not purely liquid or gaseous in nature, but, instead, also contain high fractions of solids, such as, for example, muds, slurries, oils or high viscosity media in general.

The determining of the density or the fill level of such media is performed in industrial plants not only in the static state, thus in containers, tanks or other storage facilities, but, instead, also along the transport paths of the respective media in pipelines. In these cases, the measuring arrangement, thus the radiation source as well as the detector unit, is placed on the particular pipe, through which the medium to be measured is led.

In such case, it is necessary to apply the radiation source and the detector unit using a suitable clamping apparatus in such a manner on the pipe, referred to in the following as measuring tube, that the radiation cone of the radiation source is directed toward the measuring tube, and such that the detector unit is located in the radiation cone after passage of the radiation through the measuring tube.

In the case of this configuration, however, it is possible that the radiation cone also reaches regions outside of the measuring tube. This depends firstly on the aperture angle of the radiation cone as well as the diameter of the measuring tube and relates, above all, to the lateral regions between the clamping apparatus and the measuring tube.

During operation and during servicing of the radiometric measuring arrangement, it must, however, be assured that the radiation cone of the radiation source certainly cannot reach maintenance personnel. Thus, it must be prevented that some body part of maintenance personnel gets exposed to radioactive radiation. Especially for clamping holders of the state of the art, this is, however, not automatically a given, since these are constructed, most often, to provide variable aperture angle of the radiation source and to fit different diameters of measuring tube. As a result, a secure structural integration in the clamping holder of protective elements, which make the radiation cone at least laterally inaccessible, is not possible. Rather, the measuring arrangements, which are designed for variable measuring tube diameter, are currently subsequently covered with protective means.

SUMMARY OF THE INVENTION

An object of the invention, therefore, is to provide a measuring arrangement for radiometric measurement of a medium in a measuring tube, especially for density- or fill level measurement, which blocks access to the radiation.

This object is achieved according to the invention by a measuring arrangement for radiometric density- or fill level measuring of a medium in a measuring tube with a tube axis, wherein the measuring arrangement comprises:
  a radiation source for emitting radioactive radiation toward the measuring tube with a fixed radiation cone,
  a detector unit, which detects radioactive radiation after its passage through the measuring tube,
  a clamping apparatus with a first holding plate for holding the radiation source,
  with a second holding plate for holding the detector unit, and
  with at least one connecting element, which connects the first holding plate and the second holding plate with one another in such a manner that the two holding plates are clamped tightly against the measuring tube.

In such case, there are placed on the first holding plate a first blocking element and a second blocking element in such a manner that the radiation cone is inaccessible at least laterally between the measuring tube and the first holding plate. Furthermore, there are placed on the second holding plate a third blocking element and a fourth blocking element in such a manner that the radiation cone is inaccessible at least laterally between the measuring tube and the second holding plate.

In an advantageous embodiment of the measuring arrangement, the first blocking element and/or the second blocking element are/is arranged shiftably on the first holding plate tangentially with reference to the measuring tube.

Shiftable arrangement of the blocking elements means that the first holding plate can be fitted to different measuring tube diameters. The shiftable arrangement can be provided, for example, by screwed connection of the blocking elements to the first holding plate, wherein in the case of this embodiment elongated holes can be located on the first holding plate extending tangentially to the measuring tube, in order that the screwed connection can occur variably in the tangential direction.

In an additional preferred embodiment of the invention, the third blocking element and/or the fourth blocking element are/is arranged shiftably on the second holding plate tangentially with reference to the measuring tube.

In parallel with the first holding plate, the second holding plate can by this type of embodiment be fitted to different measuring tube diameters. It can, again, be produced by screwed connection of the blocking elements on the holding plate, wherein elongated holes are located on the second holding plate extending tangentially to the measuring tube, in order that the screwed connection can occur variaby in the tangential direction.

Preferably, the first blocking element and/or the second blocking element are/is embodied as a rectangular plate with at least a first edge, which extends, for instance, orthogonally to the first holding plate. This form of embodiment represents the simplest form of embodiment of the first as well as the second blocking element, with which a shape matching, lateral blocking between the measuring tube and the first holding plate can be achieved.

Furthermore, the first edge is preferably angled over toward the measuring tube. In this way, there results in the case of rectangular plate shape of the first as well as of the second blocking element not only a lateral, shape matched blocking between the measuring tube and the first holding element. By angling the first edge over, also accessing the radiation cone between the first holding element and the measuring tube along the tube axis is prevented.

In an additional advantageous embodiment of the invention, the third blocking element and/or the fourth blocking element are/is embodied as a rectangular plate with at least a second edge, which extends, for instance, orthogonally to the second holding plate. Analogously to the first and second blocking elements, this form of embodiment of the third as well as fourth blocking element represents the simplest form of embodiment, with which a shape matched lateral blocking between the measuring tube and the second holding plate can be achieved.

Advantageously, the second edge is angled over toward the measuring tube. In this way, there results in the case of rectangular plate shape of the third as well as of the fourth blocking element not only a lateral, shape matched blocking between the measuring tube and the first holding element. By angling the second edge over, also accessing of the radiation cone between the first holding element and the measuring tube along the tube axis is prevented.

In a more extensive form of embodiment of the invention, at least one of the four blocking elements is embodied wedge shaped. By this alternative shape of the blocking elements, both a lateral blocking as well as a blocking along the tube axis between the holding element and the measuring tube is achieved.

Preferably, at least one of the two holding plates has a rectangular shape with four corner regions, with at least a third edge extending parallel to the tube axis, with an upper, fourth edge and with a lower, fifth edge, which fourth edge and fifth edge extend about tangentially to the measuring tube.

Of course, the two holding plates can alternatively also have any other orientation relative to the measuring tube and any shape other than a rectangular shape.

In an additional embodiment of the invention, for the case, in which the two holding plates are rectangular, the connecting element comprises an arrangement of four threaded rods, which arrangement screw-connects the four corner regions of the first holding plate with the four corner regions of the second holding plate in such a manner that the two holding plates are clamped tightly against the measuring tube.

Preferably, the fourth edge and/or the fifth edge of at least one of the two holding elements are/is angled over toward the measuring tube. Such an angling achieves a stiffening of the particular holding plate, in order to prevent distortion of the holding plate from the weight of the radiation source or the detector unit.

Preferably, also the third edge of at least one of the two holding elements is angled-over toward the measuring tube. Also this measure increases the distortion resistance of the particular holding plate.

In an additional embodiment of the invention, the fourth edge and the fifth edge have for the case, in which the fourth edge and the fifth edge are angled over, a cutout for adjustment to the measuring tube. The cutouts prevent shifting of the first holding plate and/or the second holding plate in the tangential direction of the measuring tube. In this way, it is assured that the correct orientation of the detector unit in reference to the radiation source is maintained.

BRIEF DESCRIPTION OF THE DRAWINGS

The subject matter of the invention will now be explained in greater detail based on an example of an embodiment in the appended drawing, the figures of which as follows.

DETAILED DISCUSSION IN CONJUNCTION WITH THE DRAWINGS

The two figures show an embodiment of the measuring arrangement 1 of the invention. Measuring arrangement 1 is composed of a measuring tube 2, a radiation source 3, a detector unit 4 and a clamping apparatus. Both figures show the same embodiment.

Figure 1:
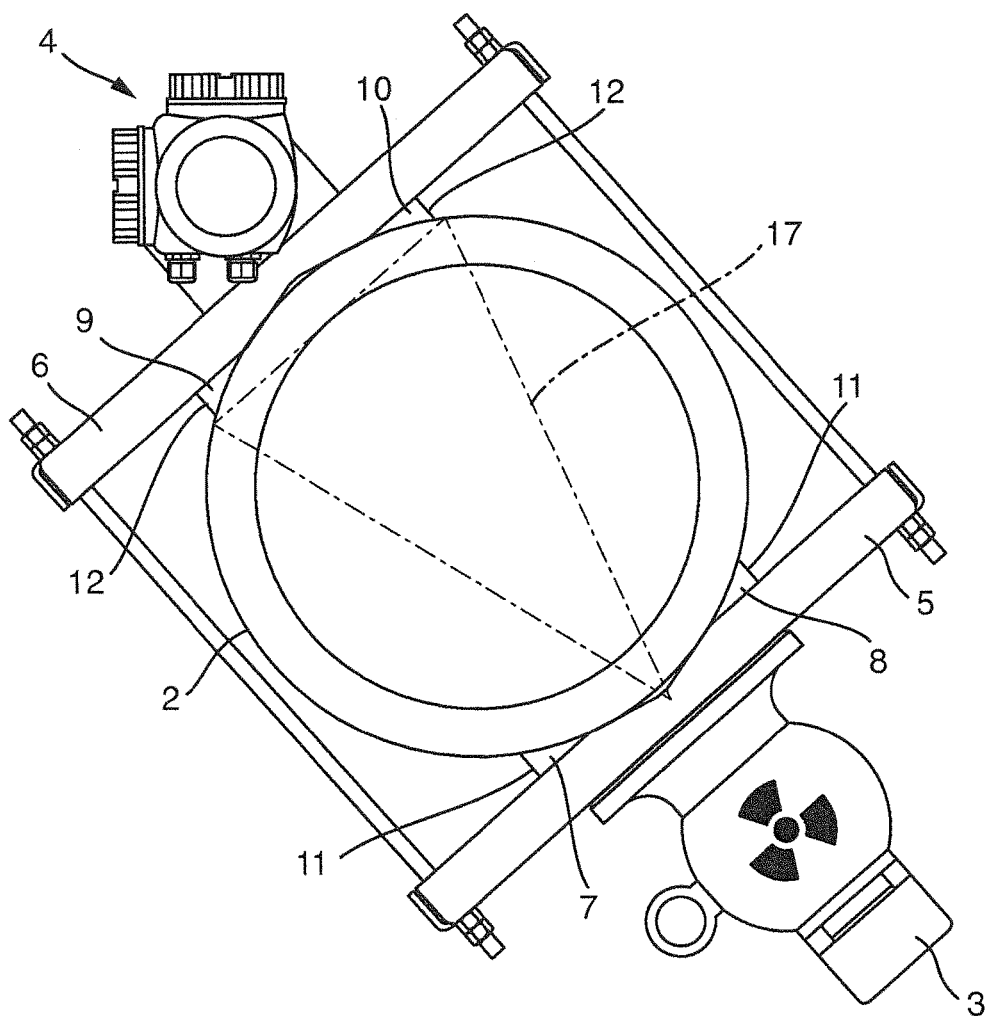
FIG. 1 is a plan view of the measuring arrangement looking in the longitudinal direction of the measuring tube.

FIG. 1 is a plan view of the measuring arrangement 1 of the invention. Measuring arrangement 1 includes a first holding plate 5 with a radiation source 3. Located on the holding plate 5 are two blocking elements 7,8. Placed on a second holding plate 6, which lies opposite the first holding plate 5 on the measuring tube 2, is a detector unit 4. Also placed on the second holding plate 6 are two more blocking elements 9,10. In the present example of an embodiment, the two holding plates 5,6 are clamped tightly against the measuring tube by an arrangement of four threaded rods. The four blocking elements 7,8,9,10 are embodied in the present example as rectangular plates with at least a first edge 11, which, for instance, extends orthogonally to the first holding plate 5, and a second edge 12, which, for instance, extends orthogonally to the second holding plate 6. In such case, the first edge 11 as well as the second edge 12 are at an angle to the measuring tube 2. By positioning the four blocking elements 7,8,9,10 on the first holding plate 5 and the second holding plate 6, the radiation cone 17 of the radiation source 3 is sealed off laterally of the measuring tube 2 and, therewith, inaccessible laterally of the measuring tube 2.

Figure 2:
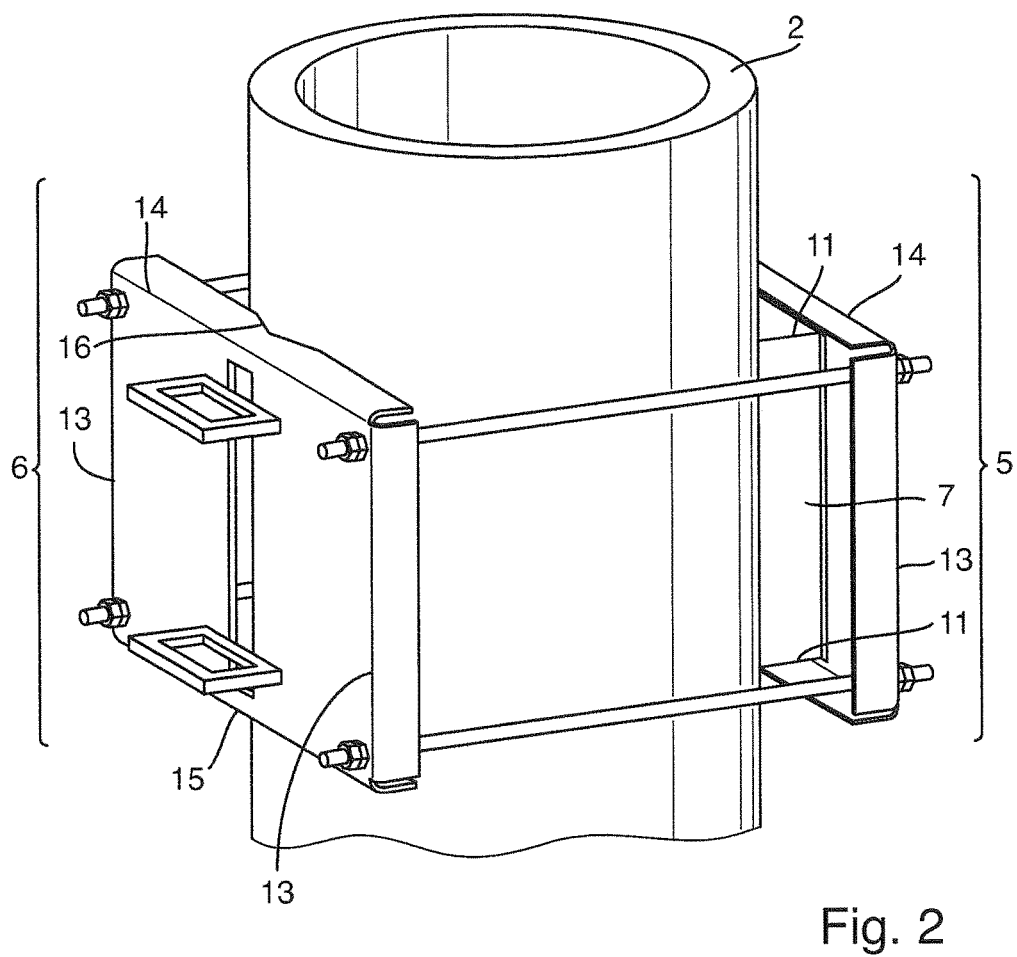
FIG. 2 is an oblique view of the clamping apparatus on the measuring tube.

FIG. 2 shows the clamping apparatus in the mounted state on the measuring tube 2. For reasons of perspicuity, the radiation source 3 and the detector unit 4 are not shown in this figure. This view shows the rectangular form of embodiment of the first holding plate 5 as well as the second holding plate 6. In the illustrated embodiment, the two holding plates 5,6 are angled over on their edges 13,14,15 for increasing distortion resistance. Likewise the upper, fourth edges 14 as well as the lower, fifth edges 15 of the two holding plates 5,6 are in the illustrated embodiment each provided with a cutout 16. Cutouts 16 avoid a shifting of the holding plates 5,6 tangentially relative to the measuring tube 2. FIG. 2 shows likewise the position of the first blocking element 7 between the measuring tube 2 and the first holding element 5. In the shown form of embodiment, the first blocking element 7 can be bolted to the first holding plate 5 through elongated holes. In such case, elongated holes directed extending tangentially to the measuring tube 2 permit a tangentially variable arrangement of the blocking elements 7,8,9,10, so that they can be fitted to different diameters of the measuring tube 2.

Of course, the inventive idea is not limited only to measuring arrangements for radiometric determination of density or the fill level, but, instead, includes any radiometric measuring arrangement on pipes.

The invention claimed is:

1. A measuring arrangement for radiometric density- or fill level measurement of a medium in a measuring tube with a tube axis, wherein the measuring arrangement comprises:
   a radiation source for emitting radioactive radiation toward the measuring tube with a fixed radiation cone;
   a detector unit, which detects radioactive radiation after its passage through the measuring tube;
   a clamping apparatus with a first holding plate for holding said radiation source; and
   a second holding plate for holding said detector unit, and with at least one connecting element, which connects said first holding plate and said second holding plate with one another in such a manner that said two holding plates are clamped tightly against the measuring tube, wherein:
   there are placed on said first holding plate a first blocking element and a second blocking element in such a manner that said fixed radiation cone is inaccessible at least laterally between the measuring tube and said first holding plate;
   there are placed on said second holding plate a third blocking element and a fourth blocking element in such a manner that said fixed radiation cone is inaccessible at least laterally between the measuring tube and said second holding plate; and
   said first blocking element and/or said second blocking element are/is embodied as a rectangular plate with at least a first edge which extends to said first holding plate.

2. The measuring arrangement as claimed in claim 1, wherein:
   said first blocking element and/or said second blocking element are/is arranged shiftably on said first holding plate tangentially with reference to the measuring tube.

3. The measuring arrangement as claimed in claim 1, wherein:
   said third blocking element and/or said fourth blocking element are/is arranged shiftably on said second holding plate tangentially with reference to the measuring tube.

4. The measuring arrangement as claimed in claim 1, wherein:
   said first edge is angled-over toward the measuring tube.

5. The measuring arrangement as claimed in claim 1, wherein:
   said second edge is angled-over toward the measuring tube.

6. The measuring arrangement as claimed in claim 1, wherein:
   at least one of said four blocking elements is embodied wedge shaped.

7. The measuring arrangement as claimed in claim 1, wherein:
   for the case, in which said two holding plates are rectangular, the connecting element comprises an arrangement of four threaded rods, which arrangement screw-connects the four corner regions of said first holding plate with the four corner regions of said second holding plate in such a manner that said two holding plates are clamped tightly against the measuring tube.

8. The measuring arrangement as claimed in claim 1, wherein:
   the fourth edge and/or the fifth edge of at least one of said two holding elements are/is angled-over toward the measuring tube.

9. The measuring arrangement as claimed in claim 8, wherein:
   the fourth edge and the fifth edge have for the case, in which the fourth edge and the fifth edge are angled over, a cutout for adjustment to the measuring tube.

10. The measuring arrangement as claimed in claim 1, wherein:
   the third edge of at least one of said two holding elements is angled-over toward the measuring tube.

* * * * *